United States Patent [19]
Mathison

[11] 4,063,447
[45] Dec. 20, 1977

[54] BRIDGE CIRCUIT WITH DRIFT COMPENSATION

[75] Inventor: Leslie C. Mathison, Houston, Tex.

[73] Assignee: Honeywell, Inc., Minneapolis, Minn.

[21] Appl. No.: 777,534

[22] Filed: Mar. 14, 1977

[51] Int. Cl.$^2$ ............................................. G01N 25/18
[52] U.S. Cl. ................................... 73/27 R; 73/23.1; 324/130
[58] Field of Search ................... 73/23.1, 27, 362 AR; 324/130; 330/146

[56] References Cited

U.S. PATENT DOCUMENTS

| | | | |
|---|---|---|---|
| 3,577,075 | 5/1951 | Krygeris | 324/130 X |
| 3,590,628 | 7/1971 | Orr | 73/23.1 |
| 3,784,912 | 1/1974 | Van Aken | 324/130 |
| 3,937,062 | 2/1976 | Rhodes, Jr. | 73/27 R |

*Primary Examiner*—Charles A. Ruehl
*Attorney, Agent, or Firm*—Laurence J. Marhoefer; Lockwood D. Burton; Mitchell J. Halista

[57] ABSTRACT

A bridge circuit having reference and measurement thermistors in respective adjacent arms is automatically readjusted to off-set any long term drift of the thermistors. The readjustment of the bridge circuit is performed between normal measurement operations using a bridge output error signal produced by the drift of the thermistors. The output signal of the bridge circuit is also applied to a comparator circuit to produce a polarity characterized output signal in response to the relative magnitude between the bridge output signal and a fixed reference signal. This characterized output signal is used to control the counting direction of an up/down counter. A source of fixed frequency pulses is connected to the input of the up/down counter during a sample window time between the measurement operations to change the count stored in the counter in accordance with the direction of counting as determined by the output signal from the comparator. The count stored in the counter, in turn, is applied to a digital to analog converter to produce an analog control signal corresponding to the digital stored count. This analog output signal is applied as a drive signal to adjustable current sources in adjacent arms of the bridge circuit to control the current through the reference and measurement thermistors whereby to offset the drift of these thermistors.

14 Claims, 2 Drawing Figures

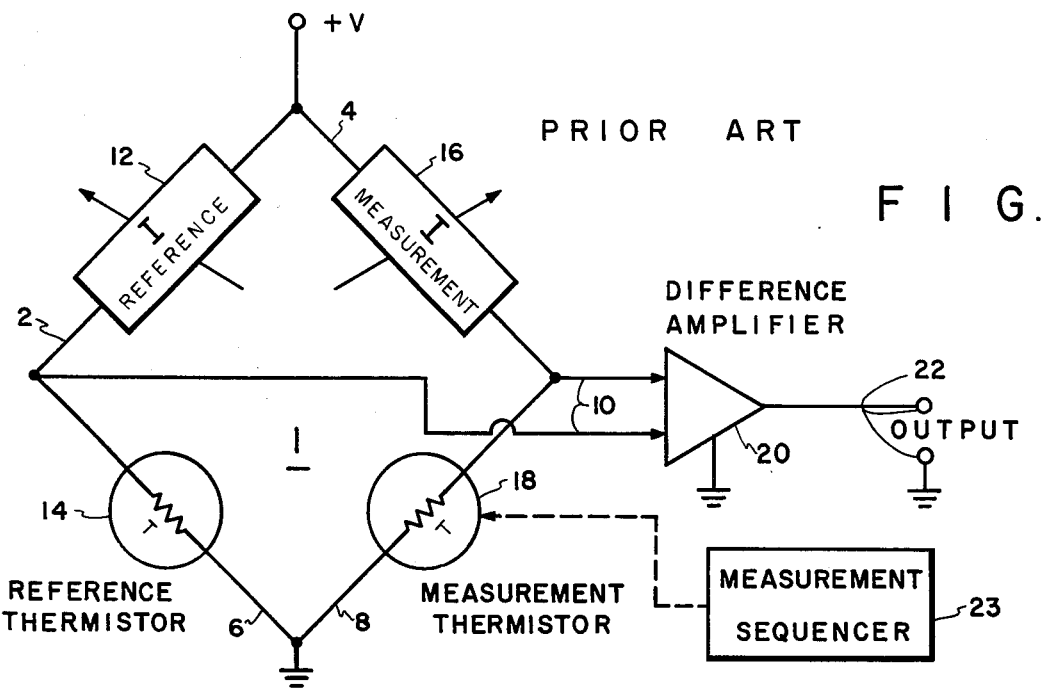
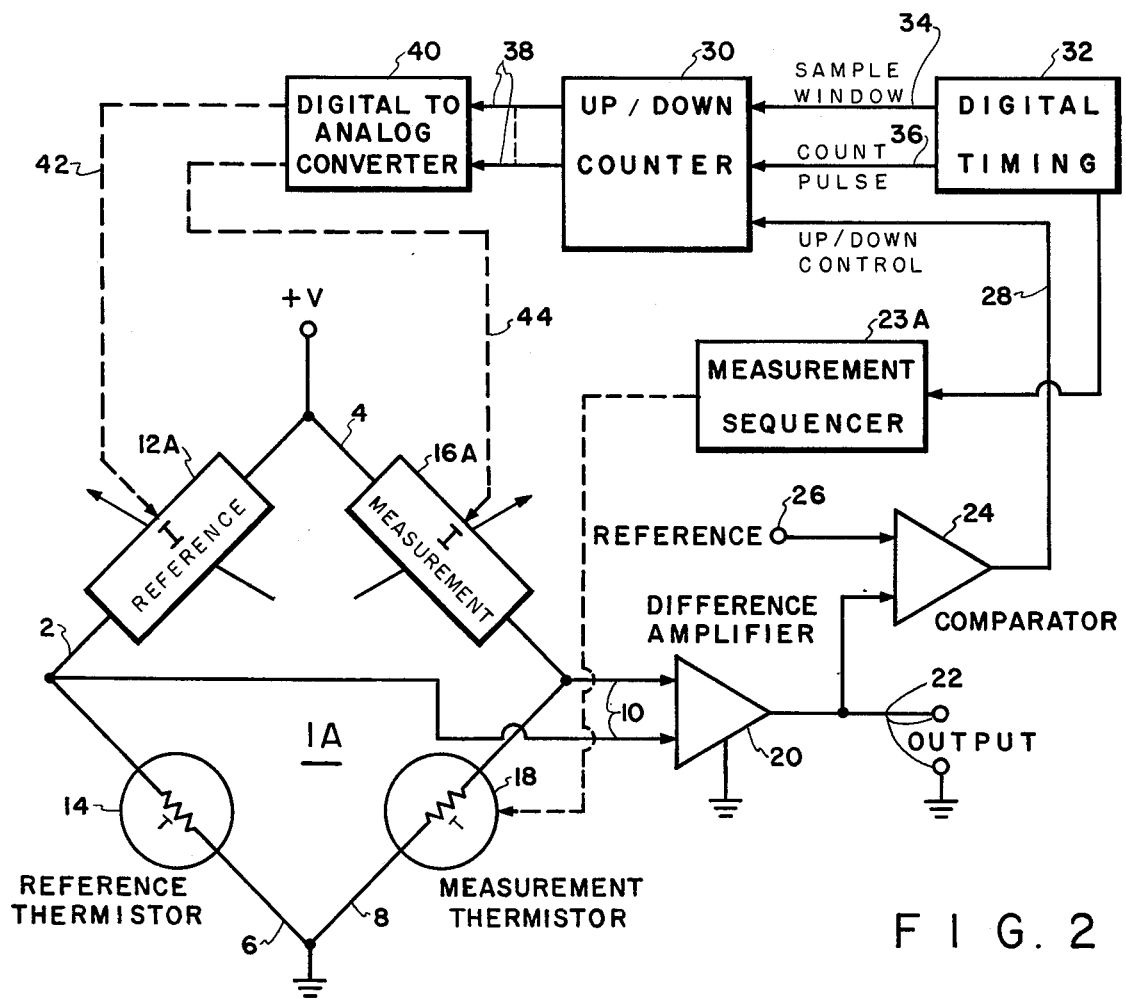

BRIDGE CIRCUIT WITH DRIFT COMPENSATION

BACKGROND OF THE INVENTION

1. Field of the Invention

The present invention relates to bridge circuits. More specifically, the present invention is directed to a bridge circuit having drift compensation.

2. Description of the Prior Art

A bridge circuit is often used in process variable measuring devices with a process variable sensitive element, or sensor, being located in one leg of the bridge whereby an output signal from the bridge is representative of a change in the measurement sensor, e.g., the gas chromatograph apparatus shown in U.S. Pat. No. 3,091,957. However, in order to provide a bridge output signal which is truly proportional only to the variations in the sensor produced by the process variable under study, the bridge circuit must be able to maintain a prior state condition in the event of a lack of a further variation in the measured process variable. In order to compensate for the usual long term drift of the bridge circuit which might be produced by the process variable responsive sensor, the prior art bridge circuit was manually readjusted before each measurement to provide a reference, or base-line, state thereof. Such a repeated manual readjustment of the conventional bridge circuit has usually prevented the resulting measurement apparatus from being directly applicable to a process monitoring system wherein it is desirable to have the monitoring system remain in a continuous operating state without the constant attendance of an operator which may be impractical as in a remote location. Accordingly, it is desirable to provide a bridge circuit having means for automatically and repeatedly compensating for drift of the bridge circuit while providing an output signal representative of a measured variable.

SUMMARY OF THE INVENTION

The object of the present invention is to provide an improved bridge circuit having means for automatically compensating for drift of the bridge circuit.

In accomplishing this and other objects, there has been provided, in accordance with the present invention, a bridge circuit having a process variable sensor in one leg thereof. An output signal from the bridge circuit obtained between measurement by the sensor of a process variable is applied to a bridge compensating circuit for automatically adjusting the bridge circuit output signal to produce a balanced state of the bridge circuit.

BRIEF DESCRIPTION OF THE DRAWING

A better understanding of the present invention may be had when the following detailed description is read in connection with the accompanying drawings, in which:

FIG. 1 is a schematic illustration of a prior art bridge circuit used to monitor a process variable, and FIG. 2 is a schematic illustration of a bridge circuit for monitoring a process variable and embodying the present invention.

DESCRIPTION OF THE PREFERRED EMBODIMENT

DETAILED DESCRIPTION

Referring to FIG. 1 in more detail, there is shown a schematic illustration of a well-known prior art bridge circuit 1 having four bridge legs 2, 4, 6 and 8. One diagonal of the bridge circuit 1 is connected between a source +V and a ground connection while the other diagonal of the bridge circuit 1 is connected to a pair of output signal lines 10. A first side of the bridge circuit 1 includes the first bridge leg 2 which includes a first current source used as a reference current source 12 and a third leg 6 of the bridge circuit 1 which includes a reference sensor, e.g., reference thermistor 14. The first and third legs 2 and 6 are connected in series between the source +V and the ground connection. A second leg 4 of the bridge circuit 1 includes a second current source used as measurement current source 16. A fourth leg 8 of the bridge circuit includes a measurement sensor, e.g., measurement thermistor 18. The second and fourth legs 4 and 8 of the bridge circuit 1 are connected in series between the source +V and the ground connection to form a second side of the bridge circuit 1. The output signal lines 10 of the bridge circuit 1 are connected to respective bridge connection points located between the first and third legs 2 and 6 and the second and fourth legs 4 and 8, respectively. The other side of the output lines 10 are connected to the input of a difference amplifier 20. The difference amplifier 20 is arranged to amplify the difference between the signals appearing on the output lines which are taken from opposite side of the bridge circuit 1 and 2 to produce a difference signal as an output signal for application to a pair of output terminals 22. A measurement sequencer 23 is used to successively apply samples of the variable being monitored to the measurement thermistor 18, e.g., in a gas chromatograph the sequencer 23 can be a valve operator cyclically controlling a sample valve to supply samples of an unknown gas between normal carrier gas flow to the measurement thermistor 18. Such sequencers are well-known in the art and may include a sampling valve, a valve drive means and a power switching means to periodically apply power to the drive means. Such prior art bridge circuits, including those wherein the sensor elements 14 and 18 thermistors, are well-known in the art, e.g., U.S. Pat. Nos. 3,100,996; 3,091,957; 3,085,431; 2,932,784 and 2,884,786. Accordingly, the operation and use of such bridge circuits and the change in response of the thermistors with time, i.e., aging, is well-known and no further explanation thereof is believed to be necessary.

In FIG. 2, there is shown a schematic illustration of a bridge circuit embodying the present invention for automatically correcting for drift of the bridge circuit. Similar reference numbers have been used for similar elements in FIGS. 1 and 2 while elements analogous to those found in FIG. 1 but differing therefrom have similar numbers followed by the letter A. Thus, the bridge circuit 1A in FIG. 2 is similar to the bridge circuit 1 shown in FIG. 1 and has a reference thermistor 14 and a measurement thermistor 18. However, the reference current source 12A in FIG. 2 for the reference thermistor 14 is arranged to be a control signal adustable device, such devices is being well-known in the art e.g., a voltage controlled semiconductor amplifier. Similarly, the measurement thermistor current source 16A is also arranged to be adjustable by analog control signals applied thereto. The drive, or control, signals for the adjustable current sources 12A and 16A are derived from the drift correction circuitry shown in FIG. 2 to provide the automatic drift correction capability of the present invention. Specifically, the output signal from the difference amplifier 20 is applied to the output terminals 22 and to a first input of a signal comparator 24. A second input signal to the signal comparator 24 is a fixed reference signal applied to a reference signal input terminal 26 connected to a second input of the comparator 24. The comparator 24 may be any suitable prior art device capable of comparing a pair of input signals and reversing the polarity of its output signal in accordance with the relative size of the compared input signals, such devices being well-known in the art.

An output signal from the comparator 24 is applied over an output line 28 as an up/down control signal to control an up/down counter 30. Thus, this control signal is applied to the up/down control input of the counter 30 to control the counting direction of the counter 30. A digital timing circuit 32 is arranged to provide fixed frequency count pulses on a count pulse line 36 connected to the count input of the up/down counter 30. The timing circuit 32 may be any suitable prior art circuit for providing a sequence of output signals, such devices being well-known in the art. Further, the timing circuit 32 provides a sample window control signal on a control line 34 to control the reception of the count pulses by the up/down counter 30, i.e., the count pulses are applied to change the stored count in the up/down counter 30 only during the duration of the sample window signal on the control line 34.

The count stored in the counter 30 is applied in parallel over digital bit count lines 38 to a digital to analog converter 40, hereinafter referred to as D/A convertor 40. The D/A convertor 40 is arranged to convert the stored digital count signal to a pair of analog output signals which are applied over respective output lines 42 and 44 to control the adjustment of the reference current and measurement current sources 12A and 16A. Alternatively, the output signal from the converter 40 may be applied only to the current source 16A for the measurement thermistor to change its output in response to an error in the bridge output signal. Changing both of the current sources 12A and 16A in opposite directions may produce a faster readjustment of the bridge circuit while adjustment of one of the current sources would permit coarser adjustment steps to be used to offset the bridge drift. The digital timing source 32 is also used to produce periodic timing signals for a measurement sequencer 23A whereby the adjustment of the current sources 12A and 16A is achieved between measurement operations by the measurement thermistor 18, i.e., the sample window signal on line 34 in applied between timing signals to the measurement sequencer 23A.

MODE OF OPERATION

While the following discussion is directed to a specific application of the present invention in correcting for the drift of a bridge circuit using thermistor elements for temperature measurements particularly in a gas chromatograph, it is to be noted that the invention disclosed herein is broadly useful in correcting for drift of bridge circuits having other applications, other types of sensors and other bridge configurations. In a gas chromatograph application as shown in the aforesaid U.S. Pat. No. 3,091,957, the measurement and reference thermistors are located in separate flow lines with the reference thermistor being exposed continuously to a carrier gas while the measurement thermistor is alternately exposed to the carrier gas and to an unknown gas to be analyzed. The response of the measurement thermistor to the unknown gas is a measure of the constituents of the gas to be analyzed.

The glass bead thermistor used in a gas chromatograph as a detector element and usually connected in an arm of a bridge circuit 1 as shown in FIG. 1 often changes its resistance value as a function of time, i.e., aging. This uncontrolled change in resistance of the thermistor causes an undesirable unbalanced condition in the bridge circuit 1 giving rise to erroneous output signals. The bridge circuit is normally set to a balanced condition, i.e., a zero level output signal, and any unbalance is effective to produce a bridge output signal. However, as the measurement thermistor changes its resistance value with time, the bridge circuit 1 becomes unbalanced and produces an error output signal which eventually, with further resistance changes, may become large enough to cause the bridge circuit 1 to be useless for its intended purpose. The bridge circuit 1 must then be manually rebalanced as shown in FIG. 1 to compensate for the thermistor drift whereby the total circuit will again be within its operating range.

The present invention is directed to a solution to this problem using the embodiment of the invention shown in FIG. 2. In general, the present invention checks a sample of the bridge output signal at a time when there is no desired, or expected, bridge output signal, i.e., between measurement operations as determined by the timing circuit 32 and the measurement sequencer 23A. If any bridge output signal is present at this sample time, it will be an error signal. This error signal is used to rebalance the bridge circuit, as discussed hereinafter. Initially the D/A converter 40 is set for mid-scale and a manual adjustment of the bridge current sources 12A and 16A is made to the desired operating range. A baseline reference signal is then applied to one input of the comparator 24 and the bridge output voltage from the difference amplifier 20 is applied to the other comparator input. The output signal from the comparator 24 provides an up/down control signal for the digital counter 30 based on whether the bridge output voltage is greater or less than the baseline reference voltage. The digital timing circuit 32 provides a sample window signal to energize the counter 30 at a time when the only signal present at the bridge output is the error signal, i.e., between measurement operations.

During the sample window signal, the timing circuit 32 also provides count pulses for the up/down counter 30 to count in the controlled direction. Thus, the counter 30 counts the count pulses during the sample window in the direction indicated by up/down control signal. The counter's digital output representing a stored count is applied to the D/A converter 40, and the converter's output signal is applied to the bridge current sources 12A and 16A. The converter output signal is used to vary the current supplied by the current sources 12A and 16A to produce either an increase or a decrease in the bridge current to ultimately change the bridge output voltage. Specifically, during the sample window, the bridge output voltage is driven toward the baseline reference voltage to reduce the output of the comparator 24. Since the D/A converter 40 is controlled in digital steps or counts, its analog output is forced to change by discrete values, or steps, causing the current from the current sources 12A and 16A and, hence, the bridge output signal voltage to change in steps. It should be noted, as previously mentioned, that it may be desirable to vary only the measurement thermistor current source 16A. Thus, the bridge output voltage level will first approach and then step past the baseline reference voltage level. This relative change causes the comparator output to change level, or polarity, to reverse the count direction of the counter 30 for the next count pulse from the timing circuit 32. The next count pulse, accordingly, causes the counter 30 to reverse by one step, which, in turn, causes the D/A converter to correspondingly change its output signal for driving the current sources 12A and 16A. Since the counter output can only change by one count the bridge output signal voltage will remain within one step of the baseline reference voltage due to the tracking characteristic of the circuit. At the end of the sample window, the count pulses from the timing circuit 32 are inhibited from affecting the counter 30, and the last count value is stored in the counter 30 until the sample window is again opened by the timing circuit 32. Between the sample windows, the bridge currents are held stable by the current sources 12A and 16A, and the bridge can be used for normal measurements. In this manner, the bridge current in the thermistors 14 and 18 is adjusted periodically whereby the bridge circuit can never become unbalanced to the point of being useless due to long term drift of the thermistors 14 and 18 or other bridge circuit components. In summary, the circuit of the present invention samples the bridge output signal during a dead, or non-measurement, time of the circuit and adjusts the bridge output signal toward a preset baseline reference by re-adjusting the bridge balance with an energizing signal representative of a bridge output signal error. At the end of the dead time, the last D/A converter output signal is held constant whereby the bridge currents do not change during the following active analysis time. This bridge circuit adjustment cycle is repeated after each analysis cycle to maintain the error-free state of the bridge circuit. A typical frequency for the count pulses could be 1H and the sample window time would be 4 seconds while measurement cycles could range from 30 seconds to 5 minutes. It should be noted that a simpler measurement system could be used wherein the combined carrier gas and sample gas are introduced to the measurement thermistor 18, and the aforesaid bridge balance is performed at a known later time when the continuously flowing carrier gas alone is being sensed, i.e., the sample gas has passed through, and before the next combined gas is introduced.

Accordingly, it may be seen that there has been provided, in accordance with the present invention, an improved bridge circuit having drift compensatng means for automatically correcting for drift of the bridge circuit.

The embodiments of the invention in which an exclusive property or privilege is claimed are defined as follows:

1. A bridge circuit apparatus comprising:
   a bridge circuit having four legs and a pair of output terminals,
   a process variable sensor connected in one leg of said bridge circuit,
   comparing means for comparing a bridge output signal on said output terminals with a reference signal to produce an output signal representative of the comparison,
   bridge output adjusting means connected in a second leg of said bridge circuit, and responsive to an energizing signal to adjust the output signal from said bridge circuit applied to said comparing means,
   control means responsive to an output signal from said comparing means for producing said energizing signal to energize said bridge output adjusting means to reduce the difference between the bridge output signal and said reference signal.

2. A bridge circuit apparatus as set forth in claim 1 wherein said process variable sensor is a thermistor and said bridge output adjusting means is a current source supplying current to said thermistor.

3. A bridge circuit apparatus as set forth in claim 1 wherein said control means includes an up/down counter, a timing signal source for supplying pulses to be counted by said counter, first circuit means for applying the output from said comparing means to said up/down counter to control the counting direction thereof, a digital to analog converter connected to said counter to convert a count stored in said counter to an analog signal, and a second circuit means for applying said analog signal as said energizing signal to said adjusting means.

4. A bridge circuit apparatus as set forth in claim 1 and including a reference sensor connected in a third leg of said bridge circuit and a second bridge output adjusting means connected in a fourth leg of said bridge circuit and responsive to an energizing signal to adjust the output signal from said bridge circuit to reduce the difference between the bridge output signal and said reference signal and wherein said energizing signal from said control means is also applied as an energizing signal to said second adjusting means.

5. A bridge circuit apparatus as set forth in claim 4 wherein said reference sensor is a thermistor and said second bridge output adjusting means is a current source supplying current to said thermistor.

6. A bridge circuit apparatus as set forth in claim 5 wherein said control means includes an up/down counter, a timing signal source for supplying pulses to be counted by said counter, first circuit means for applying the output from said comparing means to said up/down counter to control the counting direction thereof, a digital to analog converter connected to said counter to convert a count stored in said counter to an analog signal, and a second circuit means for applying said analog signal as said energizing signal to said adjusting means.

7. A bridge circuit apparatus as set forth in claim 1 and further including sequencer means for selectively exposing said sensor to a process variable to be measured and wherein said control means includes a timing signal source for successively operating said sequencer means to expose said sensor to said process variable and energizing signal producing means responsive to said timing signal source and to said output signal from said comparing means for producing said energizing signal and for adjusting said energizing signal between said successive operations of said sequencer means whereby said energizing signal is adjusted when said sensor is not exposed to said process variable.

8. A bridge circuit as set forth in claim 7 wherein said energizing signal producing means also includes an up/down counter, said timing signal source supplying pulses to be counted by said counter and a sample window signal to said counter to permit counting of said pulses between successive energizations of said sequencer means, first circuit means for applying the output from said comparing means to said up/down counter to control the counting direction thereof, a digital to analog converter connected to said counter to convert a count stored in said counter to an analog signal, and a second circuit means for applying said analog signal as said energizing signal to said adjusting means.

9. A bridge circuit apparatus as set forth in claim 8 wherein said process variable sensor is a thermistor and said bridge output adjusting means is a current source supplying current to said thermistor.

10. A bridge circuit as set forth in claim 8 and in including a reference sensor connected in a third leg of said bridge circuit and a second bridge output adjusting means connected in a fourth leg of said bridge circuit and responsive to an energizing signal to adjust the output signal from said bridge circuit to reduce the difference between the bridge output signal and said reference signal and wherein said energizing signal from said control means is also applied as an energizing signal to said second adjusting means.

11. In a gas chromatograph, a measuring circuit comprising
   a bridge circuit having four legs and a pair of output terminals,
   a process variable sensor connected in one leg of said bridge circuit,
   sequencer means for selectively exposing said sensor to a process variable to be measured by alternately supplying a carrier gas combined with an unknown gas to be measured and a carrier gas without the unknown gas to said sensor,
   comparing means for comparing a bridge output signal on said output terminals with a reference signal to produce an output signal representative of the comparison,
   bridge output adjusting means connected in a second leg of said bridge circuit and responsive to an energizing signal to adjust the output signal from said bridge circuit applied to said comparing means, and
   control means responsive to an output signal from said comparing means for producing said energizing signal to energize said bridge output adjusting means to reduce the difference between the bridge output signal and said reference signal, said control means including and up/down counter, a timing source for supplying pulses to be counted by said counter, a periodic sample window signal which is applied to said counter to enable said counter to count said pulses and an operating signal between said sample window signals for operating said sequencer means to expose said sensor to said carrier gas combined with an unknown gas, first circuit means for applying the output signal from said comparing means to said up/down counter to control the counting direction thereof, a digital to analog converter connected to said counter to convert a count stored in said counter to an analog signal and a second circuit means for applying said analog signal as said energizing signal to said adjusting means whereby said energizing signal is adjusted when said sensor is not exposed to said process variable.

12. In a gas chromatograph, a measuring circuit as set forth in claim 11 wherein said process variable sensor is a thermistor and said bridge output adjusting means is a current source supplying current to said thermistor.

13. In a gas chromatograph, a measuring circuit as set forth in claim 12 and including a reference sensor connected in a third leg of said bridge circuit and continuously exposed to a carrier gas and a second bridge output adjusting means connected in a fourth leg of said bridge circuit and responsive to an energizing signal to adjust the output signal from said bridge circuit to reduce the difference between the bridge output signal and said reference signal and wherein said energizing signal from said control means is also applied as an energizing signal to said second adjusting means.

14. In a gas chromatograph, a measuring circuit as set forth in claim 13 wherein said reference sensor is a thermistor and said second bridge output adjusting means is a current source supplying current to said reference sensor.

* * * * *